United States Patent [19]

Stanko

[11] Patent Number: 5,612,374
[45] Date of Patent: Mar. 18, 1997

[54] INHIBITING GROWTH OF MAMMARY ADENOCARCINOMA

[75] Inventor: Ronald T. Stanko, 795 Scrubgrass Rd., Pittsburgh, Pa. 15234

[73] Assignee: Ronald T. Stanko, Coraopolis, Pa.

[21] Appl. No.: 194,857

[22] Filed: Feb. 14, 1994

[51] Int. Cl.$^6$ .................................................. A61K 31/19
[52] U.S. Cl. .................................................. 514/557
[58] Field of Search .................................. 514/547, 551, 514/557

[56]  References Cited

U.S. PATENT DOCUMENTS

| 4,158,057 | 6/1979 | Stanko | 424/252 |
| 4,351,835 | 9/1982 | Stanko | 424/252 |
| 4,415,576 | 11/1983 | Stanko | 424/252 |
| 4,548,937 | 10/1985 | Stanko | 424/252 |
| 4,812,479 | 3/1989 | Stanko | 514/557 |
| 4,874,790 | 10/1989 | Stanko | 514/557 |
| 5,134,162 | 7/1992 | Stanko | 514/557 |
| 5,256,697 | 10/1993 | Miller et al. | 514/625 |
| 5,283,260 | 2/1994 | Miller et al. | 514/563 |
| 5,294,641 | 3/1994 | Stanko | 514/540 |

OTHER PUBLICATIONS

Stanko et al Pyruvate Inhibits Growth of Mammary Adeno--Carcinoma 13762 in Rats, Cancer Research 54, 1004–1007, 1994.

O'Donnell–Tormey et al., J. Exp. Med. (1987 Feb. 1) 165 (2) 500–14.

Olivotto et al., Toxicol. Pathol. (1984), 12(4), 369–73.

*Primary Examiner*—Phyllis G. Spivack
*Attorney, Agent, or Firm*—Harry B. Keck; Donald O. Nickey; Standley & Gilcrest

[57] ABSTRACT

Growth of mammary adenocarcinoma in a mammal can be inhibited by orally administering a therapeutically effective dosage of pyruvate in the form of sodium pyruvate, calcium pyruvate or organic esters of pyruvate or precursors of pyruvate.

3 Claims, 1 Drawing Sheet

INHIBITING GROWTH OF MAMMARY ADENOCARCINOMA

CROSS REFERENCE TO RELATED APPLICATIONS (If any): NONE

BACKGROUND OF THE INVENTION

Field of the Invention

This invention relates to a method for treating a mammal with pyruvic acid and its salts and esters to inhibit the growth of malignancy, the spread of malignancy and to retard DNA breaks.

Pyruvate has been described for use in retarding fatty deposits in livers (U.S. Pat. No. 4,158,057); for retarding diabetes (U.S. Pat. No. 4,874,790); for retarding weight gain (U.S. Pat. Nos. 4,812,479, 4,548,937, 4,351,835); to increase body protein concentration in a mammal (U.S. Pat. No. 4,415,576); for treating cardiac patients to increase the cardiac output without accompanying increase in cardiac oxygen demand (Ser. No. 802,062, filed Nov. 27, 1991); for extending athletic endurance (U.S. Pat. No. 4,315,835); and for retarding cholesterol increase (U.S. Pat. No. 5,134,162).

Malignancies are usually carcinoma, associated with glands, lungs, etc. or sarcoma, associated with muscle, bone. Malignancies are a major medical problem in mammals, and particularly involving humans. The adenocarcinoma is a form of malignancy (carcinoma) which is known to function predictably in rats and similarly in rats and in humans. In malignancies the DNA strands become damaged and break.

STATEMENT OF THE PRESENT INVENTION

According to the present invention, an appropriate amount of pyruvate, ingested orally or parenterally will inhibit the growth of malignancy cells and will inhibit the spread of malignancy to other sites, and will retard DNA breaks. An appropriate dose is from two to twenty weight percent pyruvate based on the carbohydrate diet of the patient or an equivalent quantity introduced parenterally into the patient.

The pyruvate may be in the form of salts or esters of pyruvic acid or as precursors of pyruvic acid. Sodium pyruvate or calcium pyruvate or mixtures thereof are useful. Alanyl pyruvate is an example of a useful pyruvate ester.

DESCRIPTION OF THE PREFERRED EMBODIMENTS

Figure 1:
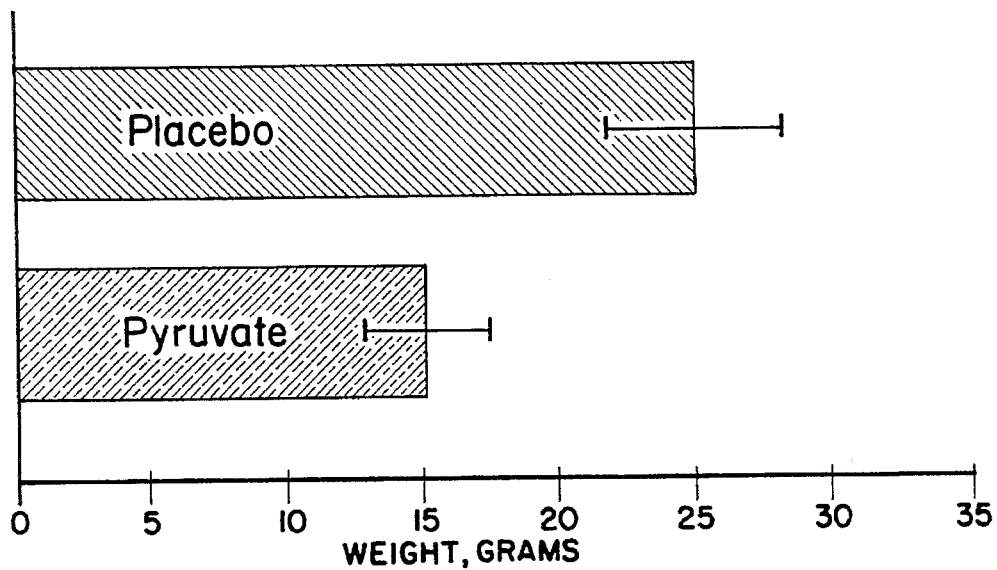
FIG. 1 is a graphical representation of malignancy weight in test animals, with and without pyruvate treatment.

Twenty-six Fischer 344 female rats weighing 140–150 grams were pair-fed for 35 days a liquid diet (35% fat, 18% protein, 47% carbohydrate, 0.0043 MJ/mL #710127 Dyets Inc. Bethlehem Pa.). The diet was iso-energetically supplemented with 37.3 grams pyruvate (22.3 grams calcium pyruvate; 15.0 grams sodium pyruvate) for the pyruvate evaluation group (13 rats) and iso-energetically supplemented with an amount of maltose-dextrin for the placebo group (13 rats). The electrolyte composition of the two diets was made equal by adding calcium carbonate or sodium citrate to the placebo diet. The feedings continued for 35 days during which the energy intake of the pyruvate group was 9.8±0.2 MJ and 1.01±0.01 MJ in the placebo group. The total pyruvate intake was 73 grams.

At the end of the 35 days, tumor cells were implanted on the backs of all of the 26 test animals. The described diets continued for 21 days thereafter.

The implanted tumor cells were 13762 Mammary Adenocarcinoma, a tumor line maintained in solid form by the National Surgical Adjuvant Breast Cancer Laboratory at the University of Pittsburgh. This tumor was selected because of its reliable growth in the Fischer rat. The fresh tumor was obtained from a subcutaneous tumor-bearing animal liver. The tissue was strained through a sieve in tissue culture medium 199 together with 1 g/L penicillin and 80 g/L streptomycin. Approximately 7 million viable cells (0.5 mL tumor suspension) were injected intradermally in the lower midline between the L2–L3 spine. Tumor growth was expected ten days following inoculation. The tumor growth was measured on day 11, 14, 18 and 21 following inoculation. The mean tumor diameter was calculated with the equation: $(\text{length} \times \text{width} \times \text{height})^{1/3}$. The animals were sacrificed on day 21. The tumor was excised; groin lymph nodes, liver and lungs were visually evaluated for gross abnormalities. Sections were recovered for further analysis, e.g., DNA breaks.

GROSS INSPECTION

An arbitrary evaluation system was developed for gross evaluation of the specimens. The tumors (malignancies) were evaluated for the necrosis and the presence of fluid. Necrosis was evaluated as:

| | |
|---|---|
| absent | 0 points |
| mild | 1 points |
| extensive | 2 points |

Fluid was evaluated as:

| | |
|---|---|
| absent | 0 points |
| trace | 1 points |
| large amount | 2 points |

Groin lymph nodes were evaluated for gross architectural changes as

| | |
|---|---|
| normal to slightly enlarged | 0 points |
| large and distorted | 1 points |
| completely distorted with extensive adhesions | 2 points |

Liver and lung metastases were evaluated as:

| | |
|---|---|
| no nodules | 0 points |
| 1–2 nodules | 1 points |
| more than 2 nodules | 2 points |

MICROSCOPIC EVALUATION

Sections of the right groin lymph node, the right lobe of the liver and a 0.5 cm² area of lung tissue with an obvious metastatic nodule were stained with hematoxylin and eosin. The large lymph nodes were evaluated for presence or absence of tumor. The liver was evaluated for presence or absence of tumor and cellular necrosis. Lung sections were scored according to the number of metastatic lesions per 0.5 mm$^2$:

| | |
|---|---|
| 1–10 | 0 point |
| more than 10 | 1 point |

Metastatic lesions were evaluated according to the number of mitotic figures per high power field. Metastatic lesions were divided into groups with:

diameter greater than 100 diameter less than 100.

The mean diameter was recorded.

STATISTICAL SUMMARY

The tumor (malignancy) growth differences between groups were analyzed, All statistical assumptions were satisfied, Differences were considered significant with $p<0.05$.

SUMMARY OF OBSERVATIONS

A mean diameter of tumor for the pyruvate group rats was 41%, 32%, 21% and 19% smaller than that of the placebo group on day 11, 14, 18 and 21 respectively. On day 21 the tumor weight was 10 grams less (40%) than the tumor weight of the placebo groups i.e., the tumor growth in the pyruvate group was significantly less than in the placebo group.

DESCRIPTION OF THE DRAWING

Figure 2:
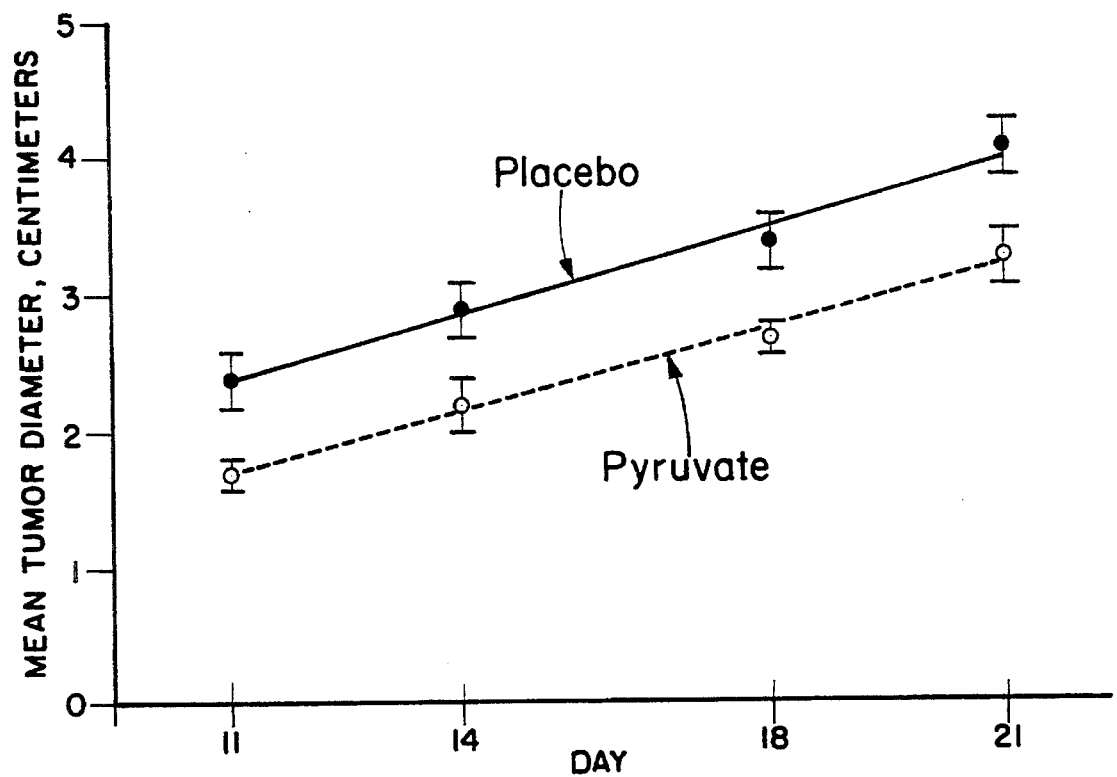
FIG. 2 is a graphical representation of the size of malignancies with time, with and without pyruvate treatment.

FIG. 1 illustrates graphically the change in mean tumor diameter for the pyruvate group and the placebo group, FIG. 2 shows that the weight of the tumors at the 21st day was significantly less in the pyruvate group than in the placebo group.

The gross appearance characteristics of the tumor, lymph nodes, liver and lungs are presented in TABLE I for the pyruvate group and the placebo group.

TABLE I

GROSS CHARACTERISTICS OF TUMOR, LYMPH NODES, LIVER AND LUNG

| | PYRUVATE GROUP | PLACEBO GROUP |
|---|---|---|
| Tumor necrosis | 0.8 ± 0.1 | 1.2 ± 0.3 |
| Tumor fluid | 0.5 ± 0.2* | 1.3 ± 0.2 |
| Lymph node architecture | 0.7 ± 0.1* | 1.2 ± 0.2 |
| Liver metastases | 0 | 0 |
| Lung metastases | 1.1 ± 0.2* | 1.9 ± 0.1 |

KEY:

| | | | |
|---|---|---|---|
| Tumor necrosis: | none = 0; | mild = 1; | extensive = 2. |
| Tumor fluid: | none = 0; | trace = 1; | large amount = 2. |

Lymph node architecture:

| | |
|---|---|
| normal to slightly enlarged node | = 0; |
| large distorted node | = 1; |
| completely distorted node, extensive adhesions | = 2. |

| | | | |
|---|---|---|---|
| Lung metastases: | none = 0; | 1–2 nodules = 1; | >2 nodules = 2. |

*p < 0.05 vs placebo

The placebo group had significantly greater tumor necrosis than the pyruvate group. The placebo group had significantly greater tumor fluid than the pyruvate group. The lymph node architecture was significantly greater for the placebo group than the pyruvate group. The lung metastases were significantly greater in the placebo group than in the pyruvate group. Neither group developed identifiable liver metastases.

Microscopic evaluation of lymph node, liver and lung are set forth in TABLE II for both groups.

TABLE II

MICROSCOPIC EVALUATION OF LYMPH NODE, LIVER AND LUNG

| | PYRUVATE GROUP - % | PLACEBO GROUP - % |
|---|---|---|
| Lymph node tumor | 85 | 53 |
| Lymph Node necrosis | 77 | 40 |
| Liver metastases | 0 | 20 |
| Liver cellular necrosis | 0* | 33 |
| Lung metastases (0) | 23 | 13 |
| Lung metastases (1–10) | 62 | 60 |
| Lung metastases (>10) | 15 | 27 |

*p < 0.05 vs placebo

The numbers reported in TABLE II are the percentage of animals with the listed findings. Lymph node tumors and lymph node necrosis were higher in the pyruvate group than in the placebo group although this difference was not significant. The pyruvate group had no liver metastases or liver cellular necrosis whereas 20% and 33% of the placebo group exhibited liver metastases and liver cellular necrosis respectively.

23% of the pyruvate group exhibited zero lung metastases and 13% of the placebo group had zero lung metastases. 62% of the pyruvate group and 60% of the placebo group exhibited lung metastases, diameter 1–10 mm. 27% of the placebo group had lung metastases greater than 10 mm whereas only 15% of the pyruvate group had lung metastases greater than 10 mm.

BREAKS IN DNA

Breaks in the single and double-strand DNA are associated with malignancy development. Paraffin sections of tumor were evaluated for DNA single and double-strand breaks using an in-situ end-labeling technique. Biotinylated nucleotides were incorporated at the breaks following addition of DNA polymerase. The number of diaminobenzidine-positive nuclei or bodies in ten fields were counted in a 100× electron, oil-immersion microscope in solid non-necrotic areas of tumor. The analysis rating (number of reported nuclei or bodies) is believed to correspond to the apoptosis. The results are set forth in TABLE III for the total breaks.

TABLE III

DNA ANALYSIS

| | PYRUVATE GROUP | PLACEBO GROUP |
|---|---|---|
| Breaks (Number) # | 8 ± 1 * | 14 ± 2 |

\# - Number of single and double strand breaks in ten fields of 100X oil-immersion objective
*p < 0.05 vs placebo.

In all three evaluations, the pyruvate group reported breaks were significantly lower than the placebo group reported breaks.

Diet consumption and weight changes were measured for the animals throughout the test.

OVERALL OBSERVATIONS

The pyruvate group received pyruvate during the preparation stage, preceding tumor implantation, and throughout the evaluation stage. The placebo group received no pyruvate at any time. Thus the results do not distinguish between pyruvate pre-tumor implantation and pyruvate post-tumor implantation. Nevertheless the results clearly show that pyruvate seems to inhibit tumor metastasis and lung metastases. Pyruvate also appears to retard the number of DNA breaks in the animals.

The reported data support a conclusion that pyruvate inhibits growth of malignancy in mammals and also inhibits the spread of malignancy from organ-to-organ and retards DNA breaks. Further the data indicate that oral administration of pyruvate inhibits growth of mammary adenocarcinoma in laboratory rats.

I claim:

1. The method of inhibiting growth of mammary adenocarcinoma in a mammal comprising introducing orally into the mammal's digestive system a therapeutically effective dose of pyruvate.

2. The method of claim 1 wherein the pyruvate is provided as 2 to 20 weight percent of the mammal's carbohydrate intake.

3. The method of claim 1 wherein the pyruvate is selected from the group consisting of sodium pyruvate, calcium pyruvate and pyruvate esters.

* * * * *